US011013506B2

(12) United States Patent
Moore

(10) Patent No.: US 11,013,506 B2
(45) Date of Patent: May 25, 2021

(54) PARTIALLY ASSEMBLED KNOTLESS SUTURE CONSTRUCT

(71) Applicant: Wright Medical Technology, Inc., Memphis, TN (US)

(72) Inventor: Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 132 days.

(21) Appl. No.: 16/155,045

(22) Filed: Oct. 9, 2018

(65) Prior Publication Data

US 2019/0125333 A1 May 2, 2019

Related U.S. Application Data

(60) Provisional application No. 62/580,218, filed on Nov. 1, 2017.

(51) Int. Cl.
*A61B 17/04* (2006.01)
*A61B 17/56* (2006.01)
(Continued)

(52) U.S. Cl.
CPC ...... *A61B 17/0401* (2013.01); *A61B 17/0469* (2013.01); *A61B 17/0487* (2013.01);
(Continued)

(58) Field of Classification Search
CPC .... A61B 2017/06185; A61B 17/06166; A61B 17/0401; A61B 2017/0403;
(Continued)

(56) References Cited

U.S. PATENT DOCUMENTS 6,066,160 A * 5/2000 Colvin ............... A61B 17/0487
606/151
7,235,091 B2 6/2007 Thornes
(Continued)

FOREIGN PATENT DOCUMENTS

EP 2238944 A2 10/2010
EP 2455002 A1 5/2012
(Continued)

OTHER PUBLICATIONS

Extended Search Report issued in connection with the corresponding European Patent Application No. 18202211.1, dated Feb. 26, 2019, 9 pages.
(Continued)

*Primary Examiner* — Wade Miles
(74) *Attorney, Agent, or Firm* — Duane Morris LLP

(57) ABSTRACT

A method for syndesmotic repair includes forming a bone tunnel through a first bone and a second bone. A partial anchoring construct is inserted through the bone tunnel. The partial anchoring construct includes a first flexible strand defining a first adjustable loop and a first anchor coupled to a first end of the first adjustable loop. A second end of the first adjustable loop is coupled to a first pull-through strand. A second anchor is coupled to the second end of the first adjustable loop after the first adjustable loop is inserted through the bone tunnel by the first pull-through strand. The length of the first adjustable loop is adjusted to position the first bone and the second bone in a predetermined spacing.

17 Claims, 17 Drawing Sheets

(51) Int. Cl.
*A61B 17/68* (2006.01)
*A61B 17/80* (2006.01)

(52) U.S. Cl.
CPC ....... *A61B 17/80* (2013.01); *A61B 2017/0404* (2013.01); *A61B 2017/044* (2013.01); *A61B 2017/0409* (2013.01); *A61B 2017/0414* (2013.01); *A61B 2017/0417* (2013.01); *A61B 2017/0475* (2013.01); *A61B 2017/0477* (2013.01); *A61B 2017/0496* (2013.01); *A61B 2017/564* (2013.01); *A61B 2017/681* (2013.01)

(58) Field of Classification Search
CPC .... A61B 2017/0404; A61B 2017/0406; A61B 2017/0408
See application file for complete search history.

(56) References Cited

U.S. PATENT DOCUMENTS

| | | | |
|---|---|---|---|
| 7,326,211 | B2 | 2/2008 | Padget et al. |
| 7,578,825 | B2 | 8/2009 | Huebner |
| 7,625,395 | B2 | 12/2009 | Muckter |
| 8,118,835 | B2 | 2/2012 | Weisel et al. |
| 8,231,674 | B2 | 7/2012 | Albertorio et al. |
| 8,398,678 | B2 | 3/2013 | Baker et al. |
| 8,506,597 | B2 | 8/2013 | Kaiser et al. |
| 8,591,578 | B2 * | 11/2013 | Albertorio ............ A61F 2/0811 623/13.13 |
| 8,814,904 | B2 | 8/2014 | Bennett |
| 8,845,686 | B2 | 9/2014 | Bennett |
| 9,138,219 | B2 | 9/2015 | Horrell et al. |
| 9,445,827 | B2 | 9/2016 | Kaiser et al. |
| 10,299,784 | B2 * | 5/2019 | Anderson .......... A61B 17/0401 |
| 2007/0239209 | A1 * | 10/2007 | Fallman ............. A61B 17/0057 606/232 |
| 2008/0071299 | A1 | 3/2008 | Allinniemi et al. |
| 2009/0054982 | A1 | 2/2009 | Cimino |
| 2009/0228049 | A1 | 9/2009 | Park |
| 2011/0106153 | A1 | 5/2011 | Stone et al. |
| 2012/0041486 | A1 | 2/2012 | Stone et al. |
| 2012/0150203 | A1 * | 6/2012 | Brady ................ A61B 17/0401 606/148 |
| 2015/0032157 | A1 | 1/2015 | Dooney, Jr. et al. |
| 2015/0039029 | A1 | 2/2015 | Wade |
| 2015/0051601 | A1 | 2/2015 | Larsen et al. |
| 2016/0030035 | A1 | 2/2016 | Zajac et al. |
| 2016/0038201 | A1 | 2/2016 | Cummings |
| 2016/0089131 | A1 | 3/2016 | Wade |
| 2016/0089189 | A1 | 3/2016 | Buscaglia et al. |
| 2016/0113691 | A1 | 4/2016 | Fritzinger et al. |
| 2016/0262814 | A1 | 9/2016 | Wainscott |
| 2016/0278828 | A1 | 9/2016 | Ragghianti |
| 2016/0287302 | A1 | 10/2016 | Horrell et al. |
| 2016/0354197 | A1 | 12/2016 | Roller et al. |
| 2017/0209140 | A1 | 4/2017 | Thornes |
| 2017/0128063 | A1 * | 5/2017 | Jackson ............. A61B 17/0401 |
| 2019/0038276 | A1 * | 2/2019 | Jackson ............. A61B 17/0401 |

FOREIGN PATENT DOCUMENTS

| | | |
|---|---|---|
| EP | 2548520 A2 | 1/2013 |
| WO | 2005041823 A1 | 5/2005 |
| WO | 2012177305 A1 | 12/2012 |
| WO | 2018111275 A1 | 6/2018 |
| WO | 2018118931 A1 | 6/2018 |

OTHER PUBLICATIONS

First Examination Report issued in connection with corresponding Australian Patent Application No. 2018247286, dated Feb. 22, 20198, 11 pages.
Porter, et al., "Optimal Management of Ankle Syndesmosis Injuries", Open Access J Sports Med, Aug. 4, 2014, pp. 173-182.
Arthrex, "Knotless Tightrope Syndesmosis Fixation" Surgical Technique, Jan. 1, 2015.
Zimmer Biomet, "ZipTight Ankle Fixation System", Soft Tissue Repair, https://www.zimmerbiomet.com/medical-professionals/foot-and-ankle/product/ziptight-fix, Sep. 27, 2018.
Office Action issued in connection with corresponding Canadian Patent Application No. 3,020,983, dated Jul. 9, 2020, 4 pages.

* cited by examiner

PARTIALLY ASSEMBLED KNOTLESS SUTURE CONSTRUCT

CROSS-REFERENCE TO RELATED APPLICATION

This application claims benefit to U.S. Provisional Application Ser. No. 62/580,218, filed Nov. 1, 2017, entitled "PARTIALLY ASSEMBLED KNOTLESS SUTURE CONSTRUCT," and which is incorporated by reference herein in its entirety.

BACKGROUND

Various injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, a first bone and a second bone must be maintained in a fixed position to allow the connective tissue to refuse.

Current suture systems include a suture anchor and one or more knots for maintaining sutures in a fixed position. Knots formed in the sutures can cause irritation during healing and may be subject to tearing due to friction or other forces applied to the knot. Current systems further require surgeons to form knots during surgery. Such systems are prone to failure and increase time of surgery.

SUMMARY

In various embodiments, a method is disclosed. The method includes a step of forming a bone tunnel through a first bone and a second bone. A partial anchoring construct is inserted through the bone tunnel. The partial anchoring construct includes a first flexible strand defining a first adjustable loop and a first anchoring element coupled to a first end of the first adjustable loop. A second end of the first adjustable loop is coupled to a first pull-through strand. A second anchoring element is coupled to the second end of the first adjustable loop after the first adjustable loop is inserted through the bone tunnel by the first pull-through strand. The length of the first adjustable loop is adjusted to position the first bone and the second bone in a predetermined spacing.

In various embodiments, a system is disclosed. The system includes a first flexible strand defining a first adjustable loop extending between a first end and a second end. The first flexible strand defines a first strand passage and a second strand passage. The first strand passage and the second strand passage have a predetermined spacing. Each of the first strand passage and the second strand passage are sized and configured to receive a portion of the first flexible strand therethrough. A first anchor is coupled to the first end of the first adjustable loop. A first pull-through strand is coupled to the first adjustable loop defined by the first flexible strand. The pull-through strand is configured to pass the first flexible strand through a bone tunnel formed in a first bone and a second bone.

In various embodiments, a system is disclosed. The system includes a partial anchoring construct. The partial anchoring construct includes a first flexible strand defining a first adjustable loop extending between a first end and a second end. The first flexible strand defines a first strand passage and a second strand passage. The first strand passage and the second strand passage have a predetermined spacing. Each of the first strand passage and the second strand passage are sized and configured to receive a portion of the first flexible strand therethrough. A first anchor includes a base and an extension extending from a first portion of the base to a second portion of the base to define a strand channel between the extension and the base. The first anchor is coupled to the first end of the first adjustable loop by passing the first flexible strand through the strand channel. A pull-through strand defines a loop extending through the first adjustable loop of the first flexible strand. The pull-through strand is configured to pass the first flexible strand through a bone tunnel formed in a first bone and a second bone. The system further includes a second anchor configured to be coupled to the second end of the first adjustable loop after insertion of the first flexible strand through the bone tunnel.

In various embodiments, a method is disclosed. The method includes a step of forming a bone tunnel through a first bone and a second bone. A bone plate is coupled to the first bone by inserting at least one plate anchor through an anchor hole defined in the bone plate. The bone plate defines a construct hole and is coupled to the first bone such that the construct hole is concentric with the bone tunnel. A partial anchoring construct is inserted through the construct hole and the bone tunnel. The partial anchoring construct includes a first flexible strand defining a first adjustable loop and a first anchoring element coupled to a first end of the first adjustable loop. A second end of the first adjustable loop is coupled to a first pull-through strand. The pull-through strand is configured to be inserted through the construct hole and the bone tunnel prior to the first adjustable loop. A second anchoring element is coupled to the second end of the first adjustable loop after the first adjustable loop is inserted through the bone tunnel by the first pull-through strand. The length of the first adjustable loop is adjusted to position the first bone and the second bone in a predetermined spacing.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
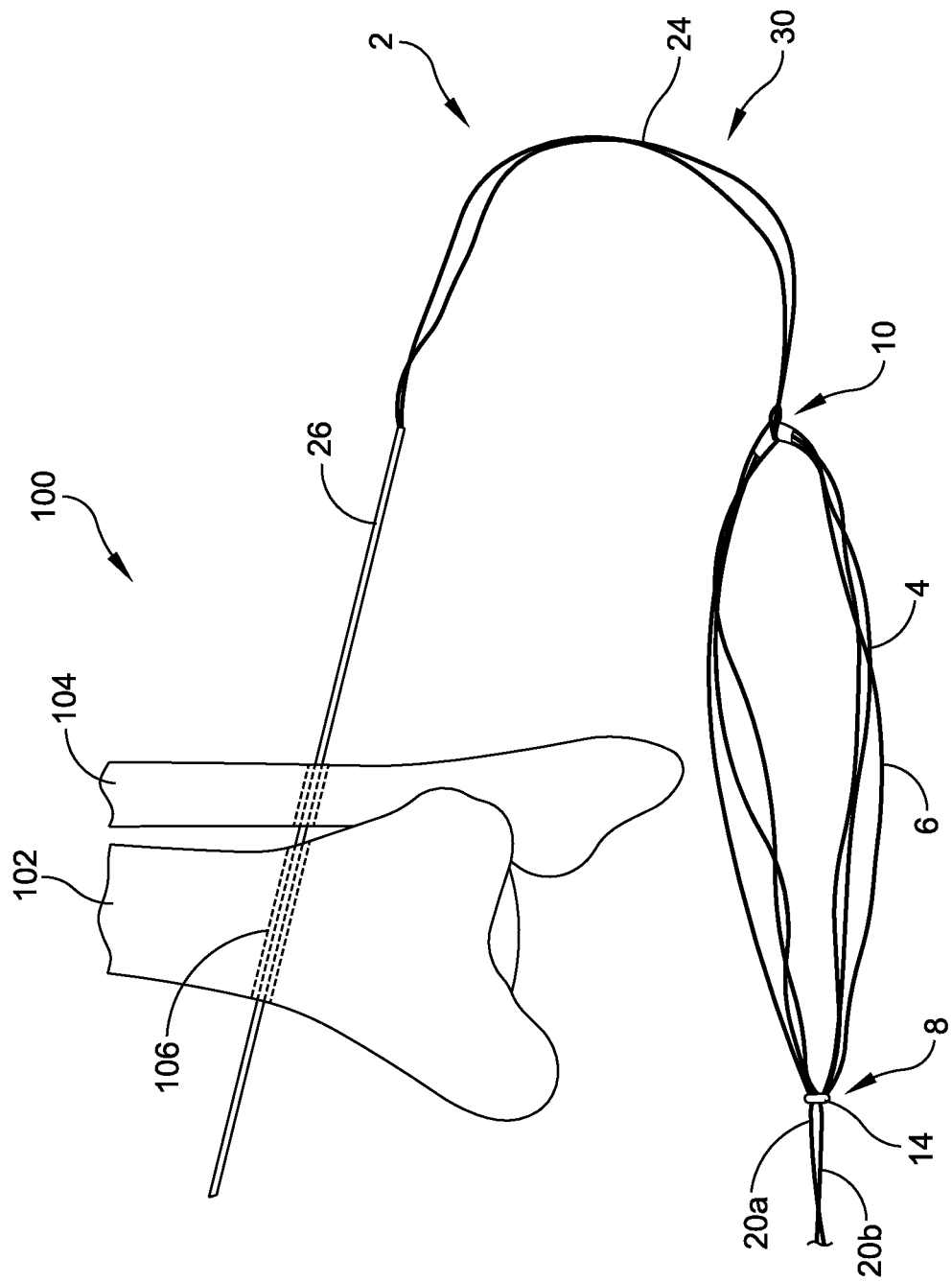
FIG. 1 illustrates a surgical site including an anchoring system configured to position a first bone and a second bone at a predetermined spacing, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a system for syndesmotic repair is disclosed. The system includes a partial anchoring construct having a first flexible strand defining at least one flexible loop. The adjustable loop is configured to be inserted through a bone tunnel defined in a first bone and a second bone. In some embodiments, the first flexible strand includes a first strand passage and a second strand passage. A first anchor is coupled to a first end of the adjustable loop. The first anchor is configured to couple the first end of the adjustable loop to an outer sursurface of the first bone at a first end of the bone tunnel. The system further includes a second anchor configured to be coupled to a second end of the adjustable loop after the second end is passed through the bone tunnel. The adjustable loop is tightened prior to position the first bone and the second bone in a predetermined spacing and maintain the first bone and the second bone within a predetermined range of movement.

FIG. 1 illustrates a surgical site 100 including a first bone 102 and a second bone 104, in accordance with some embodiments. A syndesmotic anchoring system 2 is configured to position the first bone 102 and a second bone 104 at a predetermined spacing and/or maintain the first bone 102 and the second bone 104 within a predetermined range of motion. The anchoring system 2 includes a partial anchoring construct 30 including a flexible strand 4 defining an adjustable loop 6 extending from a first end 8 to a second end 10. The flexible strand 4 can include any suitable material, such as, for example, one or more sutures, ribbons, ropes, etc. The adjustable loop 6 is configured to extend at least from a first end 106a of the bone tunnel 106 to a second end 106b. Although embodiments are discussed herein having a syndesmotic anchoring system 2 coupled to a first bone 102 and a second bone 104, it will be appreciated that the syndesmotic anchoring systems 2 disclosed and described herein can be used with any number of bones, including, for example, one bone, two bones, three bones, etc., and are within the scope of this disclosure. For example, the anchoring system of the present disclosure may be used in one bone, when the bone has at least one fracture and it is necessary to maintain the bones in a predetermined alignment or range of motion.

In some embodiments, the partial anchoring construct 30 includes a first anchor 14 coupled to a first end 8 of the adjustable loop 6. The first anchor 14 can include any suitable anchor, such as a button, a knot capsule, a fastener, and/or any other suitable anchor. For example, in some embodiments, the first anchor 14 includes a flat button having one or more openings configured to receive a portion of a flexible loop 6 therethrough and sized and configured to abut the first bone 102. The first anchor 14 retains the first end 8 of the adjustable loop 6 at a first end 106a of the bone tunnel 106. A flat button is described in greater detail below with reference to FIG. 15. In other embodiments, the first anchor 14 includes a base and extension extending from the base. The extension defines a strand passage sized and configured to receive the flexible strand 4 therethrough. In some embodiments, the extension is sized and configured to be at least partially inserted into the bone tunnel 106. A knot capsule having a base and an extension is described in greater detail below with reference to FIG. 16.

A first free end 20a and a second free end 20b of the flexible strand 4 extend from one end 8, 10 of the adjustable loop 6. The free ends 20a, 20b are configured to shorten (e.g., tighten) and/or lengthen (e.g., loosen) the adjustable loop 6. In various embodiments, the first free end 20a and the second free end 20b are configured to extend from a first end 106a of the bone tunnel 106, extend from a second end 106b of the bone tunnel 106, and/or extend from both the first end 106a and the second end 106b of the bone tunnel 106.

In some embodiments, a pull-through strand 24 is coupled to the second end 8 of the adjustable loop 16. The pull-through strand 24 is sized and configured to be inserted through the bone tunnel 106. The pull-through strand 24 can include any suitable material, such as, for example, one or more sutures, ribbons, ropes, etc. The pull-through strand 24 is coupled to the second end 10 of the adjustable loop 6, for example, by tying the pull-through strand 24 to the adjustable loop 6, by looping the pull-through strand 24 through the adjustable loop 6, and/or any other suitable coupling method. In some embodiments, the pull-through strand 24 is omitted.

In some embodiments, a guide element 26 is coupled to the pull-through strand 24. The guide element 26 is sized and configured to be inserted through the bone tunnel 106. The guide element 26 is resilient and is configured to be inserted through the bone tunnel 106 without deforming. For example, the guide element 26 can include a needle, stent, guide wire, k-wire, and/or any other suitable guide element 26. In some embodiments, the guide element 26 can include a self-drilling guide element configured to form the bone tunnel 106 simultaneously with insertion of the guide element 26 through the first bone 102 and the second bone 104, such as a k-wire. In some embodiments, the pull-through strand 24 is omitted and the guide element 26 is directly coupled to the second end 10 of the adjustable loop 6.

In some embodiments, the syndesmotic anchoring system 2 includes a second anchor 16. The second anchor 16 can include a button anchor, a knot capsule, a fastener, and/or any other suitable anchor. For example, in some embodiments, the second anchor 16 includes a button anchor having one or more openings configured to receive a portion of a flexible loop 6 therethrough and sized and configured to abut the second bone 104 to retain the second end 10 of the adjustable loop 6 at a second end 106b of the bone tunnel 106. The second anchor 16 couples the second end 10 of the adjustable loop 6 to the second bone 104 at a second end of the bone tunnel 106. The second anchor 16 can be coupled to the second end 10 of the adjustable loop 6 prior to, during, and/or after the adjustable loop 6 has been shortened (e.g., tightened).

Figure 2:
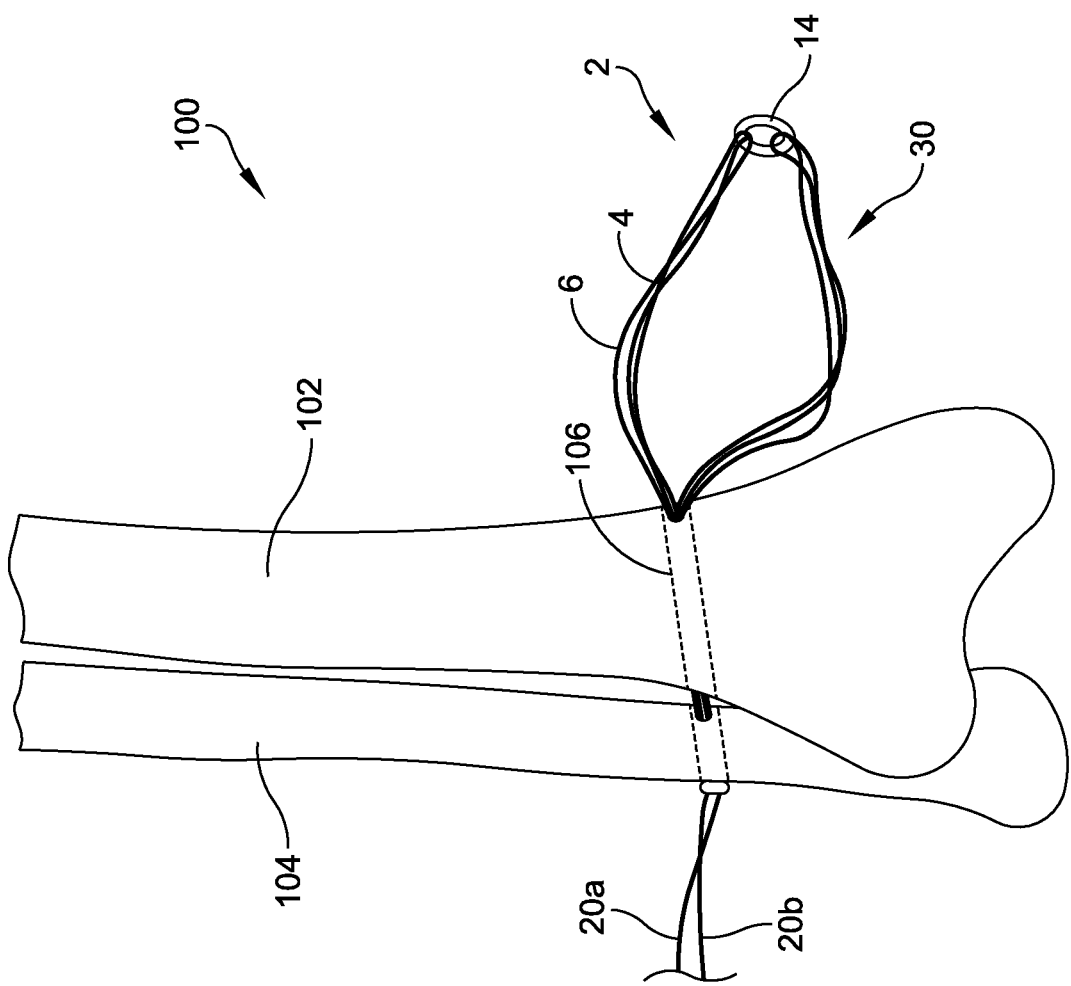
FIG. 2 illustrates the surgical site of FIG. 1 including a partial anchoring construct of the anchoring system having an adjustable loop inserted through the first bone and the second bone, in accordance with some embodiments.
Figure 3:
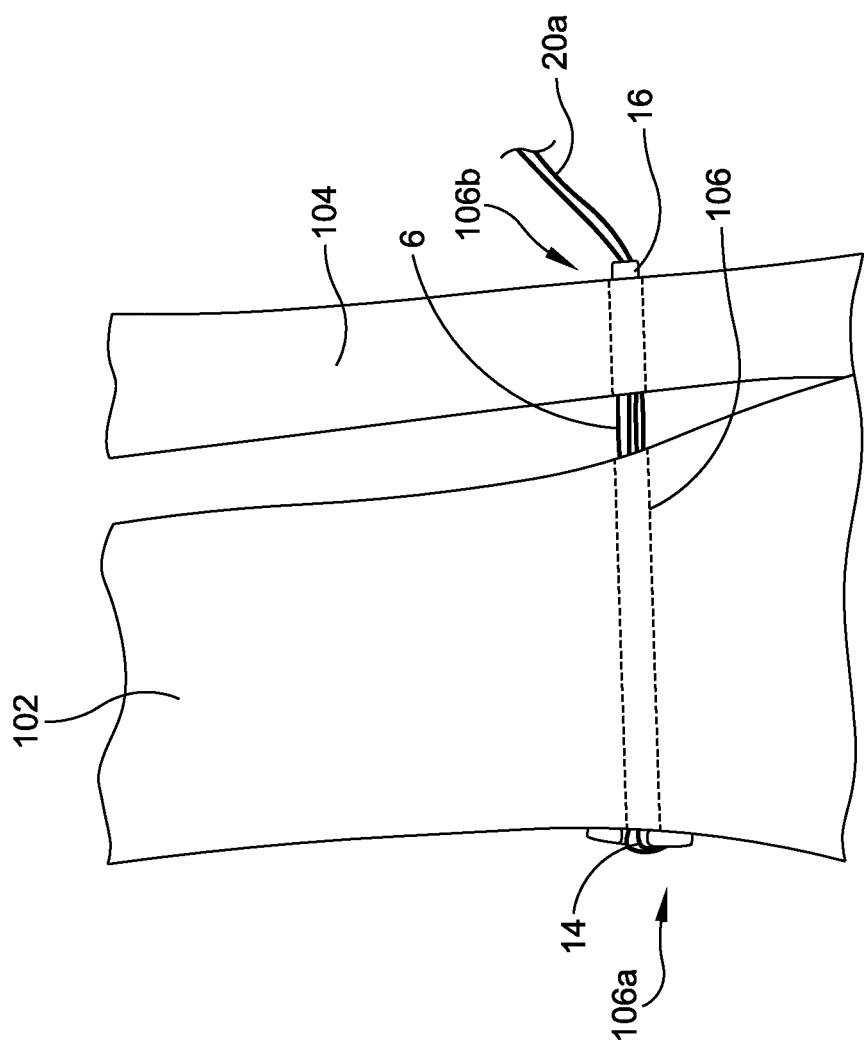
FIG. 3 illustrates the surgical site of FIG. 2 having a first anchor and a second anchor coupled to the partial anchoring construct, in accordance with some embodiments.

FIG. 2 illustrates the partial anchoring construct 30 after being inserted through the first bone 102 and the second bone 104, in accordance with some embodiments. The guide element 26 (and a pull-through suture 24, if present) is disconnected after insertion through the bone tunnel 106. For example, in some embodiments, the pull-through strand 24 is cut to release the pull-through strand 24 and the guide element 26 from the adjustable loop 6, although it will be appreciated that the pull-through strand 24 and/or the guide element 26 can be release from the adjustable loop 6 using any suitable method. After inserting the adjustable loop 6 through the bone tunnel 106, the free ends 20a, 20b, which are positioned outside of bone tunnel 106, are pulled to shorten the adjustable loop 6. The second anchor 16 is coupled to the second end 10 of the adjustable loop 6 to couple the second end 10 to the second bone 104. The adjustable loop 6 can be further shortened to position the first bone 102 and the second bone 104 in a selected spacing.

The adjustable loop 6 can be shortened prior to, simultaneously with, or after coupling the second anchor 16 to the second end 10 of the adjustable loop 6.

Figure 4:
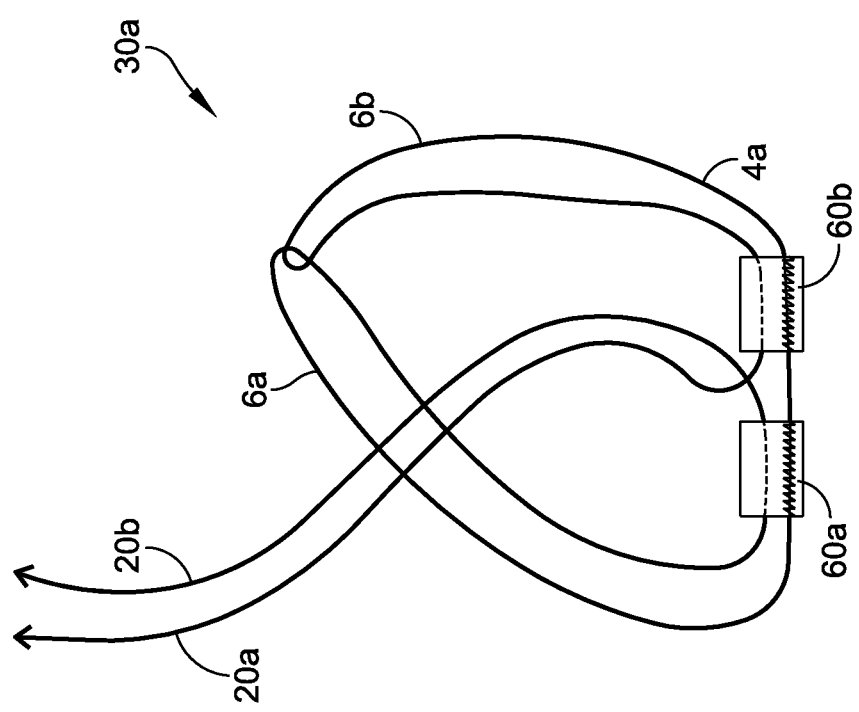
FIG. 4 illustrates a partial anchoring construct including a first strand passage and a second strand passage, in accordance with some embodiments.

FIG. 4 illustrates a partial anchoring construct 30a including flexible strand 4a defining a plurality of adjustable loops 6a, 6b extending through strand passages 60a, 60b, in accordance with some embodiments. The partial anchoring construct 30a is similar to the partial anchoring construct 30 described above, and similar description is not repeated herein. The flexible strand 4a includes a first strand passage 60a and a second strand passage 60b. The strand passages 60a, 60b include a flexible material defining a channel or passage 52a, 52b. The flexible material can include a similar material to the flexible strand 4a and/or a different material. The strand passages 60a, 60b can be formed integrally with the flexible strand 4a, can be coupled to the flexible strand 4a, and/or can be freely moveable with respect to the flexible strand 4a.

In some embodiments, a first end 20a of the flexible strand 4a is passed through a first strand passage 60a to define a first adjustable loop 6a and a second end 20b of the flexible strand 4a is passed through a second strand passage 60b to define a second adjustable loop 6b. The first and second adjustable loops 6a, 6b can be interlocked (e.g., the first adjustable loop 6a is looped through the second adjustable loop 6b). In some embodiments, the first strand passage 60a and the second strand passage 60b have a predetermined spacing therebetween sized and configured to receive the first anchor 14 therein, as discussed in greater detail with respect to FIGS. 7-10.

Figure 5:
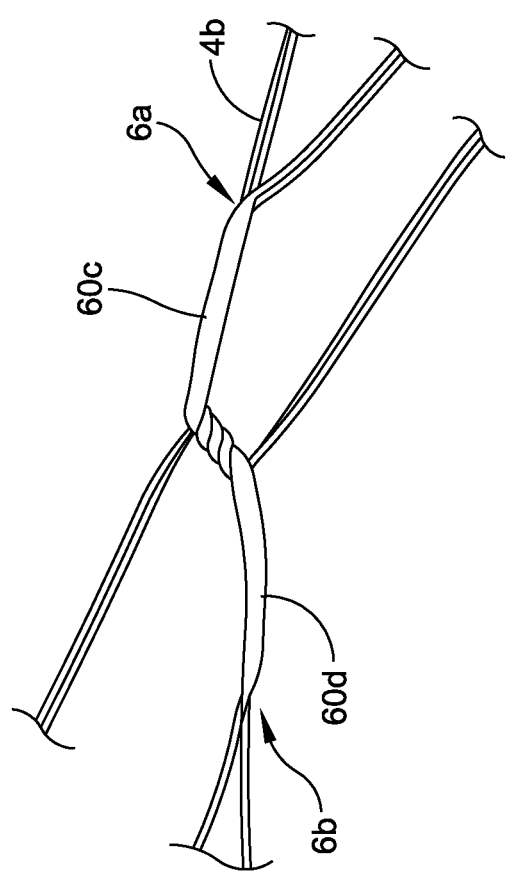
FIG. 5 illustrates a flexible strand including a first woven passage and a second woven passage, in accordance with some embodiments.

FIG. 5 illustrates a flexible strand 4b defining a first woven passage 60c and a second woven passage 60d, in accordance with some embodiments. The flexible strand 4b is similar to the flexible strand 4a described above, and similar description is not repeated herein. The first and second woven passages 60c, 60d include a first portion of the flexible strand 4b that is woven about a second portion of the flexible strand 4b to define each of the strand passages 60c, 60d having a portion of the flexible strand 4b extending therethrough. In some embodiments, the woven passages 60c, 60d are self-tightening when a predetermined force is applied to the flexible strand 4b. For example, in some embodiments, the woven passages 60c, 60d are configured to constrict as force is applied to the free ends 20a, 20b of the flexible strand 4b. When the force exceeds a predetermined threshold, the woven passages 60c, 60d are constricted such that the flexible strand 4b extending through the woven passages 60c, 60d is locked in place.

Figure 16:
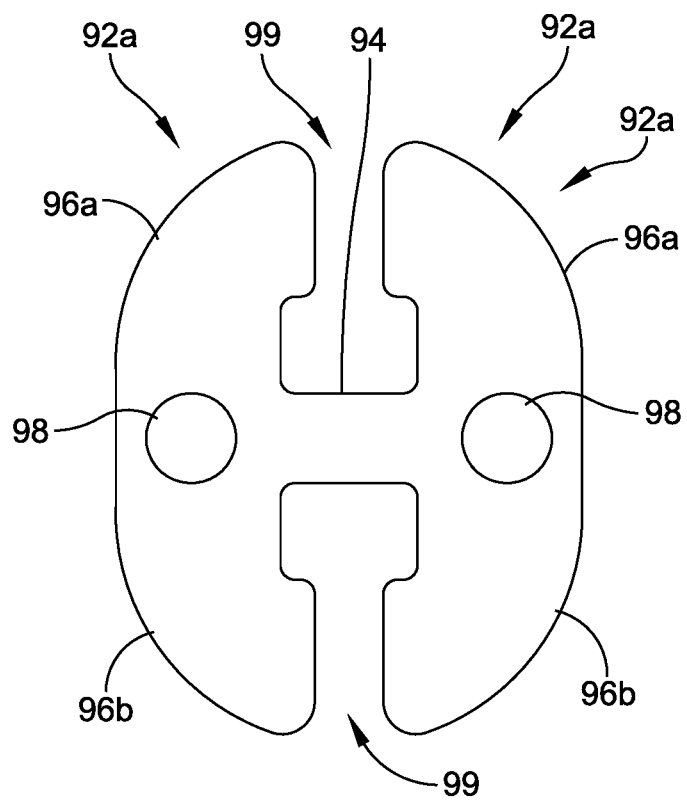
FIG. 16 illustrates a flat button, in accordance with some embodiments.

FIG. 16 illustrates a flat button anchor 90, in accordance with some embodiments. The flat button anchor 90 can be used as a first anchor 14 and/or a second anchor 16 with respect to the syndesmotic anchoring system 2. The flat button anchor 90 includes a first side 92a and a second side 92b coupled by a center post 94. Each of the first side 92a and the second side 92b include a first arm 96a and a second arm 96b extending at a predetermined arc from the center post 94. Each of the arms 96a, 96b define cutouts 99 sized and configured to receive a portion of an adjustable loop 6 thereabout. The flat button anchor 90 is configured to couple a distal end of an adjustable loop 6 to a second bone 104.

In some embodiments, a flat button anchor 90 is coupled to the second end 10 of the adjustable loop 6 after being passed through the bone tunnel 106. In some embodiments, the flat button anchor 90 defines a plurality of holes 98 sized and configured to receive an adjustable loop 6 and/or flexible strand 4 therethrough. In other embodiments, the flat button anchor 90 includes one or more cutouts 99 configured to receive a portion of the flexible strand 4 therethrough. The cutouts 99 are sized and configured to receive the flexible strand 4 but prevent passage of the strand passages 60a, 60b therethrough. Although specific embodiments are illustrated, it will be appreciated that the flat button anchor 90 can include any suitable combination of openings for receiving the flexible strand 4 therethrough.

Figure 17:
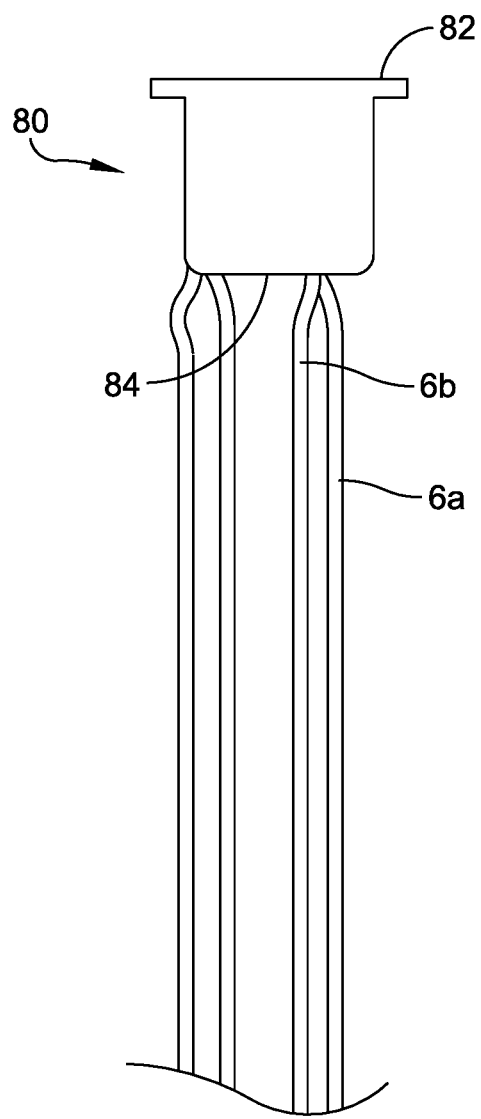
FIG. 17 illustrates a knot capsule, in accordance with some embodiments.

FIG. 17 illustrates a knot capsule anchor 80, in accordance with some embodiments. The knot capsule anchor 80 can be used as a first anchor 14 and/or a second anchor 16 with respect to the syndesmotic anchoring system 2. The knot capsule 80 includes a base 82 and an extension 84 extending therefrom. The extension 84 defines a strand passage sized and configured to receive a flexible strand 4 therethrough. In some embodiments, the extension 84 is sized and configured to be inserted at least partially within the bone tunnel 106. Knot capsules are described in greater detail in International Patent Application PCT/US16/66902, which is incorporated herein by reference in its entirety.

Figure 6:
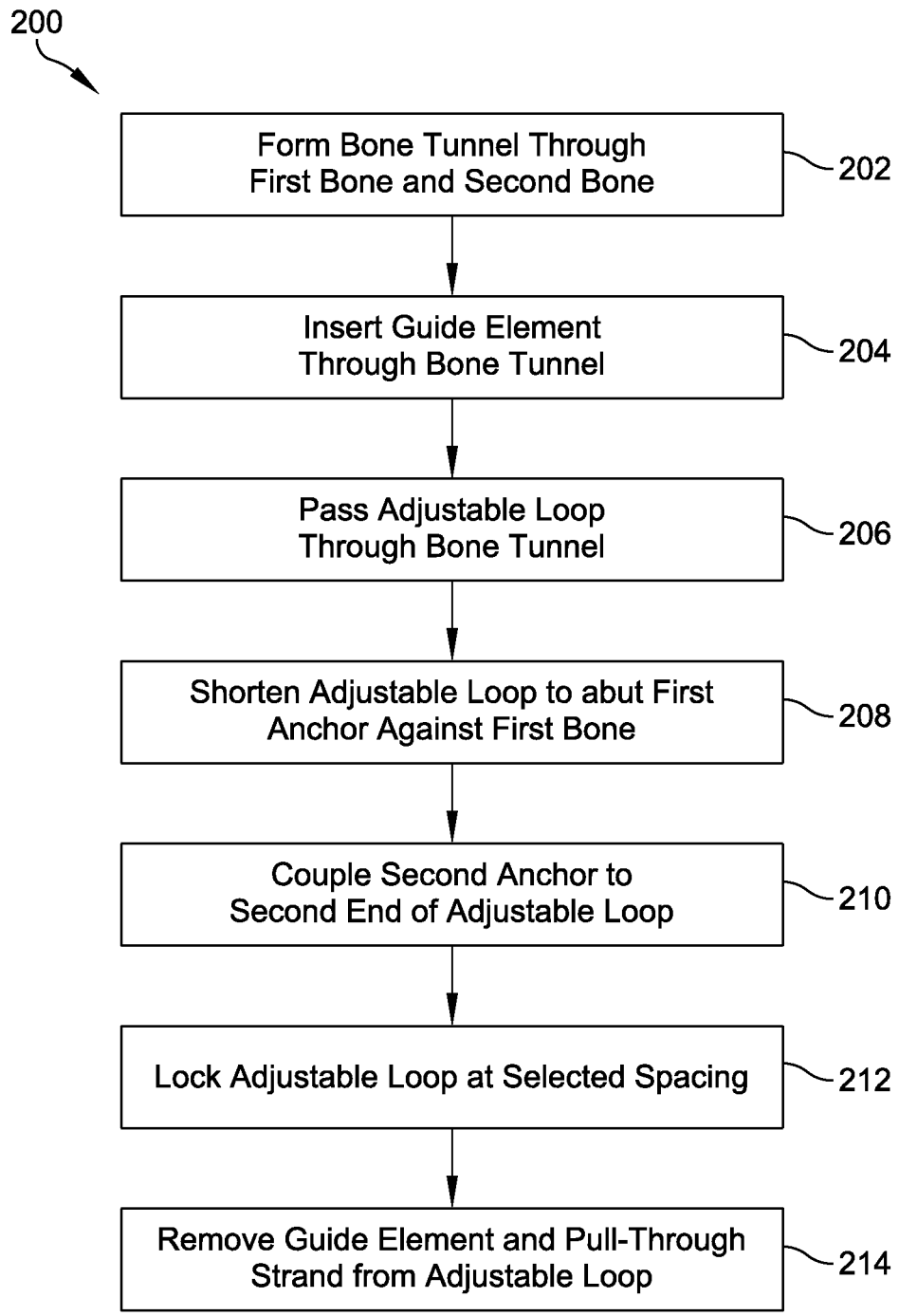
FIG. 6 is a flowchart illustrating a method of positioning a first bone and a second bone in at a predetermined spacing, in accordance with some embodiments.

FIG. 6 is a flowchart illustrating a method 200 of syndesmotic repair using the syndesmotic system 2 described above, in accordance with some embodiments. At step 202, a bone tunnel 106 is formed through a first bone 102 and a second bone 104. The bone tunnel 106 can be formed by any suitable instrument, such as, for example, a drill, a k-wire, a reamer, and/or any other suitable instrument. Although step 202 is illustrates as an independent step in method 200, it will be appreciated that the formation of the bone tunnel 106 can occur simultaneously and/or integrally with one or more additional steps discussed below.

At step 204, a guide element 26 is inserted through the bone tunnel 106 from a first side 106a to a second side 106b. The guide element 26 is coupled to a second end 10 of an adjustable loop 6 of a partial anchoring construct 30. The guide element 26 can be coupled to the adjustable loop 6 by a pull-through strand 24 and/or can be directly coupled to the adjustable loop 6. The guide element 26 can include any suitable resilient element configured to be inserted through the first bone 102 and the second bone 104, such as a needle, k-wire, etc. In some embodiments, the guide element 26 is configured to form the bone tunnel 106 simultaneously with insertion through the first bone 102 and the second bone 104 such that step 202 and step 204 are performed as a single step.

At step 206, the adjustable loop 6 is passed through the bone tunnel 106 by the guide element 26. At step 208, a first anchor 14 coupled to a first end 8 of the adjustable loop 6 is abutted against a first side of the first bone 102. The first anchor 14 can include any suitable anchor, such as a button, a knot capsule, a fastener, and/or any other suitable anchor. The first anchor 14 can be coupled to the adjustable loop 6 prior to and/or after insertion of the adjustable loop 6 through the bone tunnel 106. In some embodiments, the first anchor 14 is sized and configured to be positioned between a first strand passage 60a and a second strand passage 60b formed in the flexible strand 4. The first anchor 14 can be abutted against the first bone 102 by passing the adjustable loop 6 through the bone tunnel 106 and/or by shortening the adjustable loop 6.

At step 210, a second anchor 16 is coupled to the second end 10 of the adjustable loop 6. The second anchor 16 can include any suitable anchor, such as a button, a knot capsule, a fastener, and/or any other suitable anchor. At step 212, the adjustable loop 6 is shortened (e.g., tightened) to abut the second anchor 16 against an outer sursurface of the second bone 104. The adjustable loop 6 is further shortened to position the first bone 102 and the second bone 104 in a predetermined spacing. The adjustable loop 6 can be shortened by applying a force to a first free end 20a and/or a second free end 20b extending from the bone tunnel 106.

Figure 12:
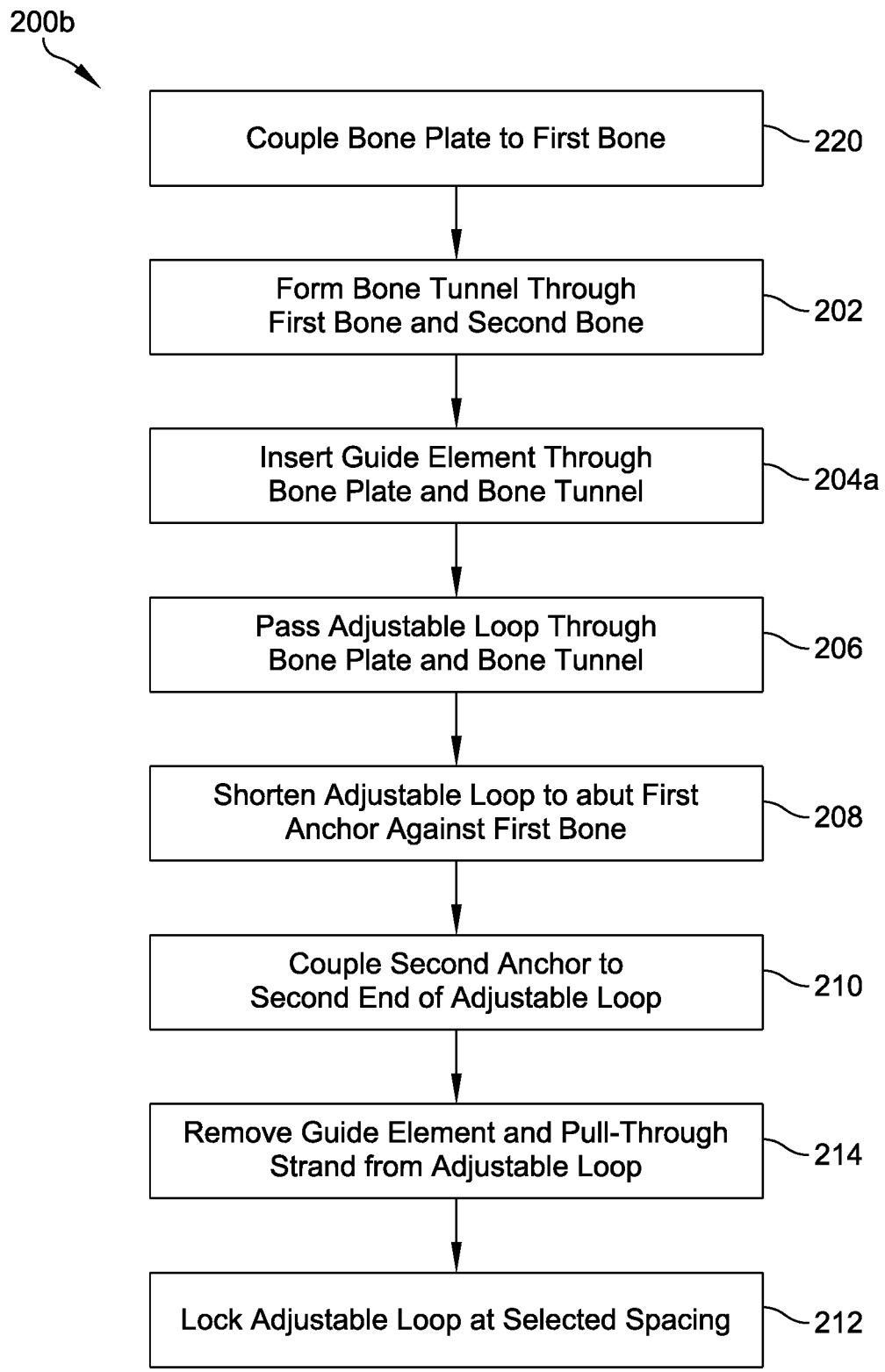
FIG. 12 is a flowchart illustrating a method of maintaining a first bone and a second bone in a correct anatomical position, in accordance with some embodiments.

At step 212, the adjustable loop 6 is locked or fixed at a selected spacing. For example, in some embodiments, a knot is formed in the first free end 20a and/or the second free end 20b to maintain the adjustable loop 6 in a fixed position. In other embodiments, the first anchor 14 and/or the second anchor 16 can include a self-locking anchor, such as a knot capsule containing a self-locking knot configured to apply a locking force to the adjustable loop 6 when a predetermined force (corresponding to a predetermined spacing of first and second bones 102, 104) is applied to the flexible strand 4. Although specific embodiments are discussed herein, it will be appreciated that the adjustable loop 6 can be fixed at a selected length using any suitable method. At step 214, after passing the second end 10 of the adjustable loop 6 through the bone tunnel 106, the guide element 26 (and the pull-through strand 24, if present) is removed from the second end 10 of the adjustable loop 6. The pull-through strand 24 and/or the guide element 26 can be removed using any suitable method, such as, for example, cutting the pull-through strand 24, cutting a portion of the flexible strand 4, and/or any other suitable method. Although embodiments are discussed herein having a disclosed order of steps, it will be appreciated that the one or more of the steps of method 200 may be completed one or more additional and/or alternative orders (for example, as illustrated in FIG. 12) and are within the scope of this disclosure.

Figure 7:
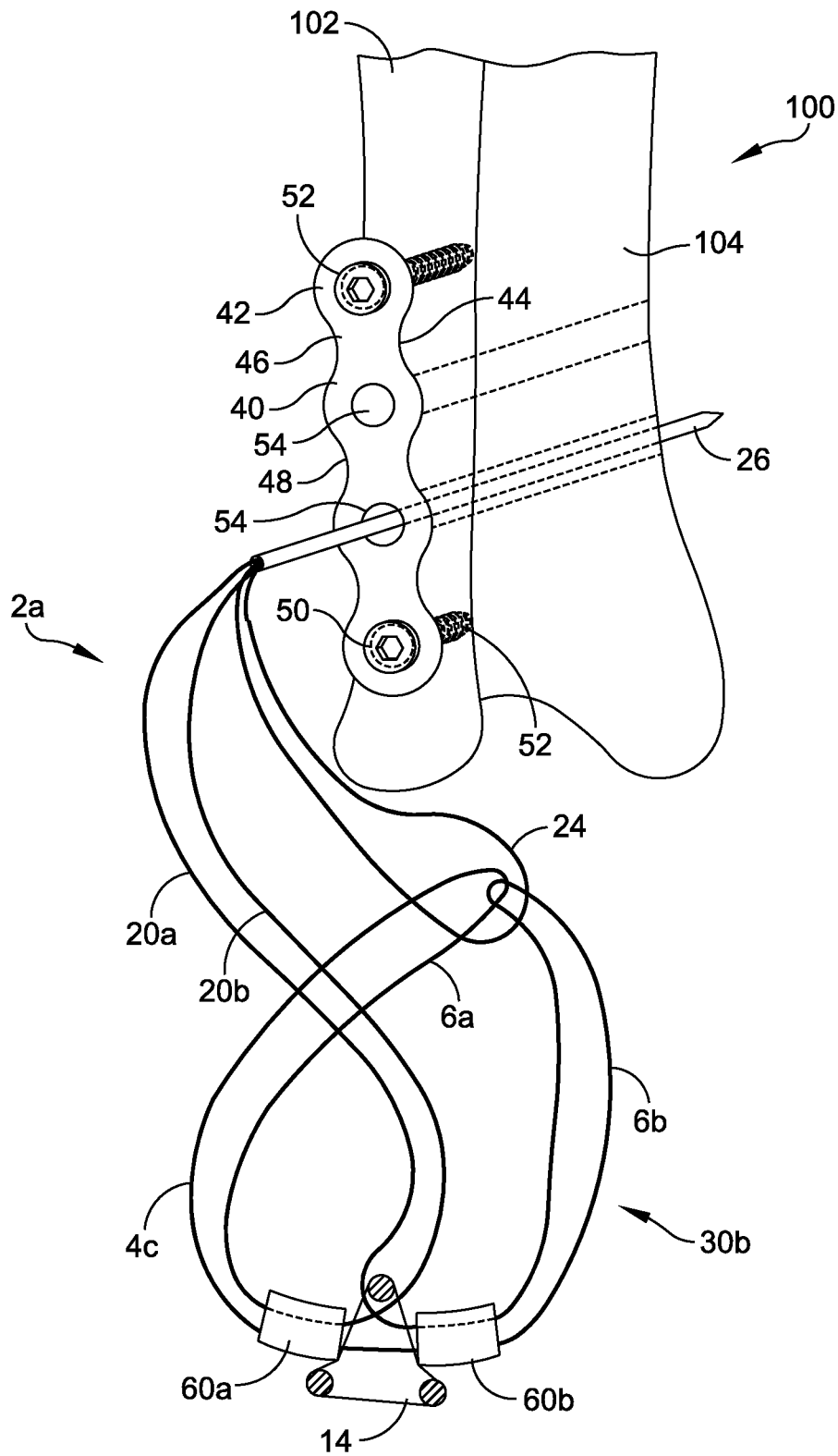
FIG. 7 illustrates a surgical site having an anchoring system including a bone plate and a partial anchoring construct having first and second adjustable loops configured to be inserted through a first bone and a second bone, in accordance with some embodiments.
Figure 8:
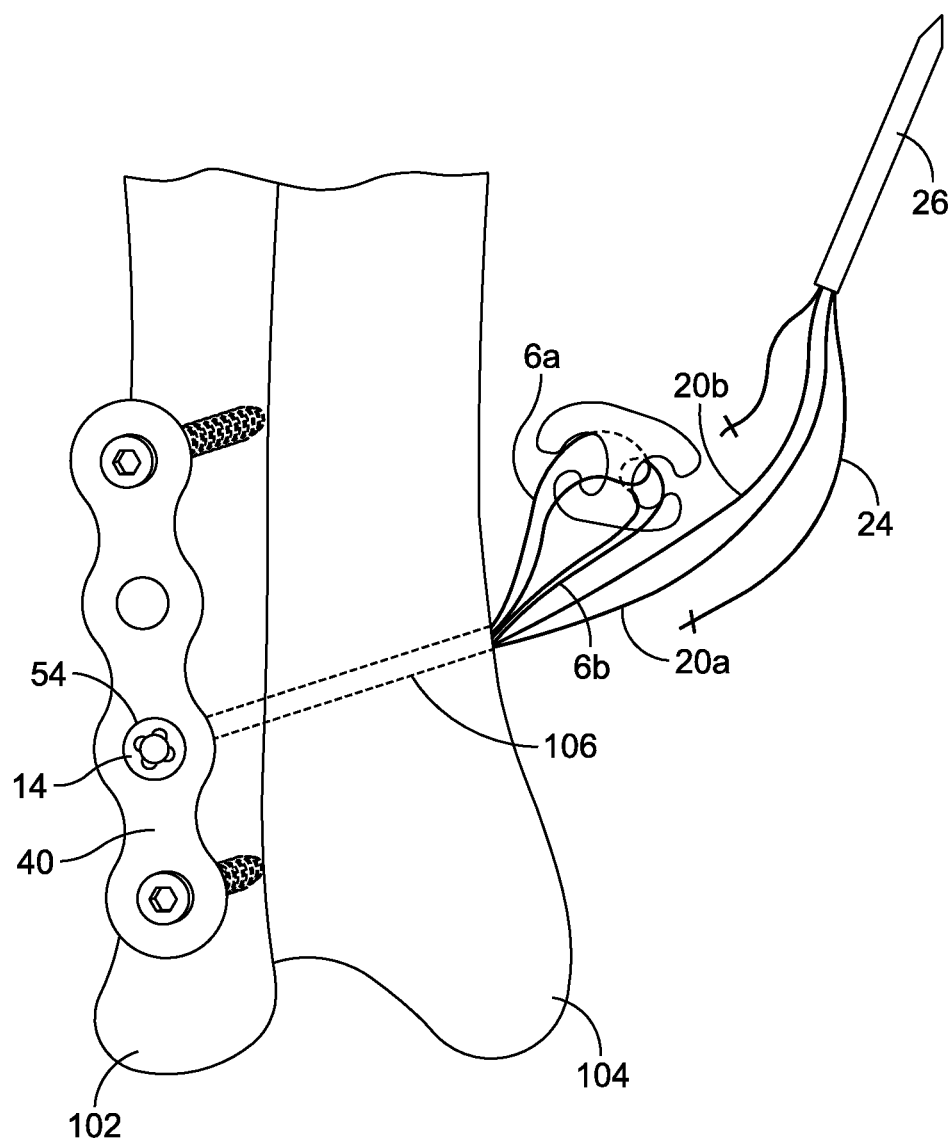
FIG. 8 illustrates the surgical site of FIG. 7 having the adjustable loop inserted through the first bone and the second bone, in accordance with some embodiments.
Figure 9:
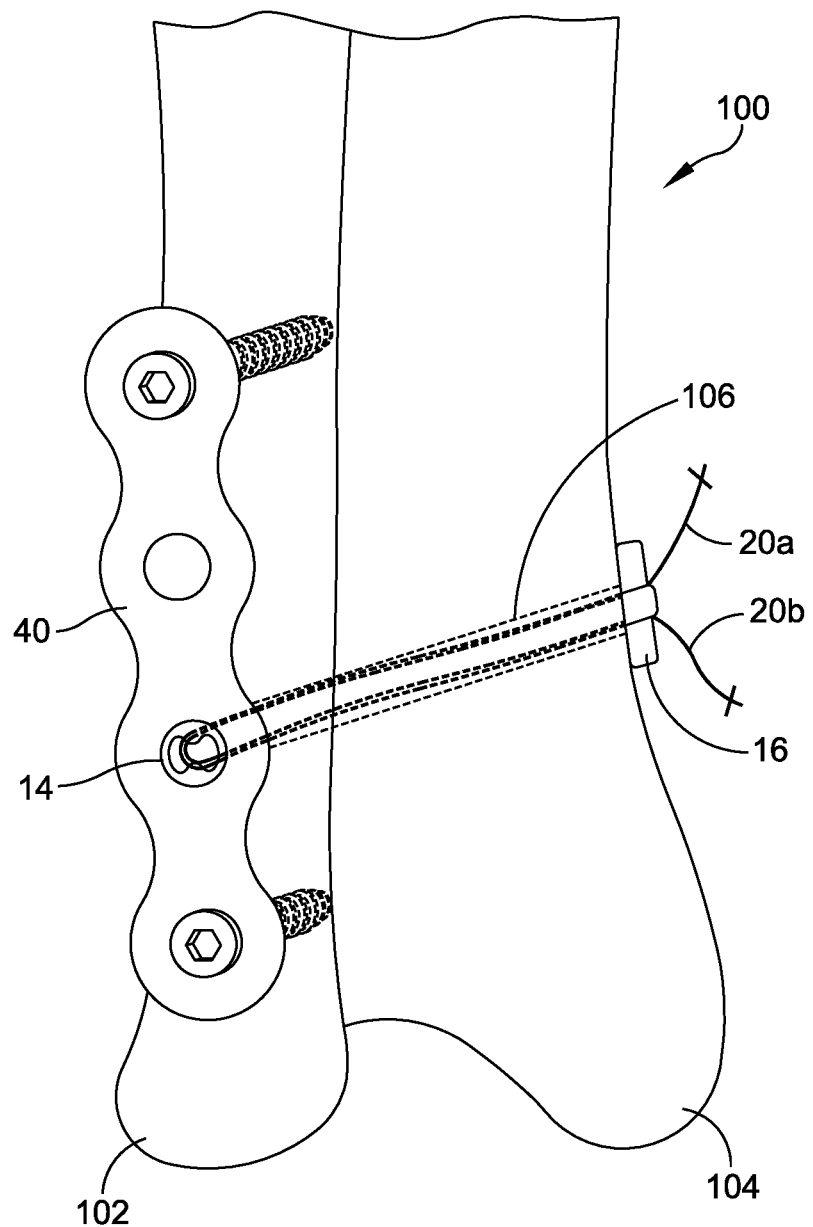
FIG. 9 illustrates the surgical site of FIG. 8 having a first anchor and a second anchor coupled to the partial anchoring construct, in accordance with some embodiments.

FIGS. 7-9 illustrate a syndesmotic anchoring system 2a including a bone plate 40, in accordance with some embodiments. The syndesmotic anchoring system 2a is similar to the syndesmotic anchoring system 2 discussed above, and similar description is not repeated herein. The syndesmotic anchoring system 2a includes a bone plate 40. The bone plate 40 is sized and configured to abut one of the first bone 102 or the second bone 104. The bone plate 40 includes a body 42 extending between a bone facing surface 44 and an opposite surface 46 and defined by a perimeter 48. One or more fastener holes 50 can extend between the bone facing surface 44 and the opposite surface 46. The one or more fastener holes 50 are sized and configured to receive fasteners 52 therethrough. The fasteners 52 can include any suitable fastener, such as a screw, pin, k-wire, etc., configured to couple the bone plate 40 to a selected one of the first bone 102 or the second bone 104. Further, fasteners 52 can be locking, non-locking, or poly-axial screws.

The bone plate 40 defines at least one construct hole 54. Each construct hole 54 is sized and configured to receive a portion of the partial anchoring construct 30b therethrough. The construct holes 54 are configured to be aligned with a bone tunnel 106 formed in the first and second bones 102, 104 when the bone plate 40 is coupled to one of the first bone 102 or the second bone 104. In some embodiments, the construct hole 54 includes a countersink sized and configured to receive at least a portion of the first fastener 14 and/or a second fastener 16 therein. For example, in some embodiments, the construct hole 54 includes a countersink sized and configured to receive a first anchor 14 including a flat button therein such that the flat button is flush with the opposite surface 46 of the bone plate 40 when the partial anchoring construct 30 is tightened (see FIG. 8.)

In some embodiments, the flexible strand 4c includes a first strand passage 60a and a second strand passage 60b. A first end 20a of the flexible strand 4c is passed through the first strand passage 60a to define a first adjustable loop 6a and a second end 20b of the flexible strand 4c is passed through a second strand passage 60b to define a second adjustable loop 6b. The first and second adjustable loops 6a, 6b can be interlocked (e.g., the first adjustable loop 6a is looped through the second adjustable loop 6b.)

In some embodiments, the first strand passage 60a and the second strand passage 60b are spaced apart such that the first anchor 14 may be positioned between the first and second strand passages 60a, 60b. The first anchor is adjacent to each of the first and second strand passages such that no portion of the strand passages 60a, 60b extend into or through the first anchor 14. For example, in some embodiments, the spacing between the strand passages 60a, 60b is selected such that the first strand passage 60a and the second strand passage 60b are positioned immediately adjacent to (and on opposite sides of) the first anchor 14 when the first anchor 14 is positioned between the strand passages 60a, 60b and coupled to the flexible strand 4c. In other embodiments, the strand passages 60a, 60b are positioned adjacent to and spaced apart from the first anchor 14 when the first anchor 14 is coupled to the flexible strand 4c.

As shown in FIG. 7, in some embodiments, the free ends 20a, 20b of the adjustable loop 6 and the pull-through suture 24 are coupled to a guide element 26, such as a k-wire shuttle. The free ends 20a, 20b and the pull-through suture 24 are passed from a first side 106a of the bone tunnel 106 to a second side 106b. The guide element 26 is passed through one of the construct holes 54 formed in the bone plate 40 prior to being passed through the first bone 102 and the second bone 104. The guide element 26 is passed through the bone tunnel 106 to draw the free ends 20a, 20b, pull-through suture 24, and adjustable loops 6a, 6b into the bone tunnel 106. The guide element 26 is advanced out of the bone tunnel 106 to extend free ends 20a, 20b and pull-through suture 24 from a second end 106b of the bone tunnel 106. The guide element 26 and/or the pull-through suture 24 can be further advanced away from the bone tunnel 106 such that a second end 10 of each of adjustable loops 6a, 6b extend from the second end 106b of the bone tunnel 106. In some embodiments, a second anchor 16 can be coupled to the second end 10 of each of the adjustable loops 6a, 6b. The guide element 26 can be disconnected from the free ends 20a, 20b and the pull-through suture 24, for example by cutting the free ends 20a, 20b and the pull-through suture 24, prior to, during, and/or after coupling the second anchor 16 to the second end 10 of the adjustable loops 6a, 6b.

Figure 10:
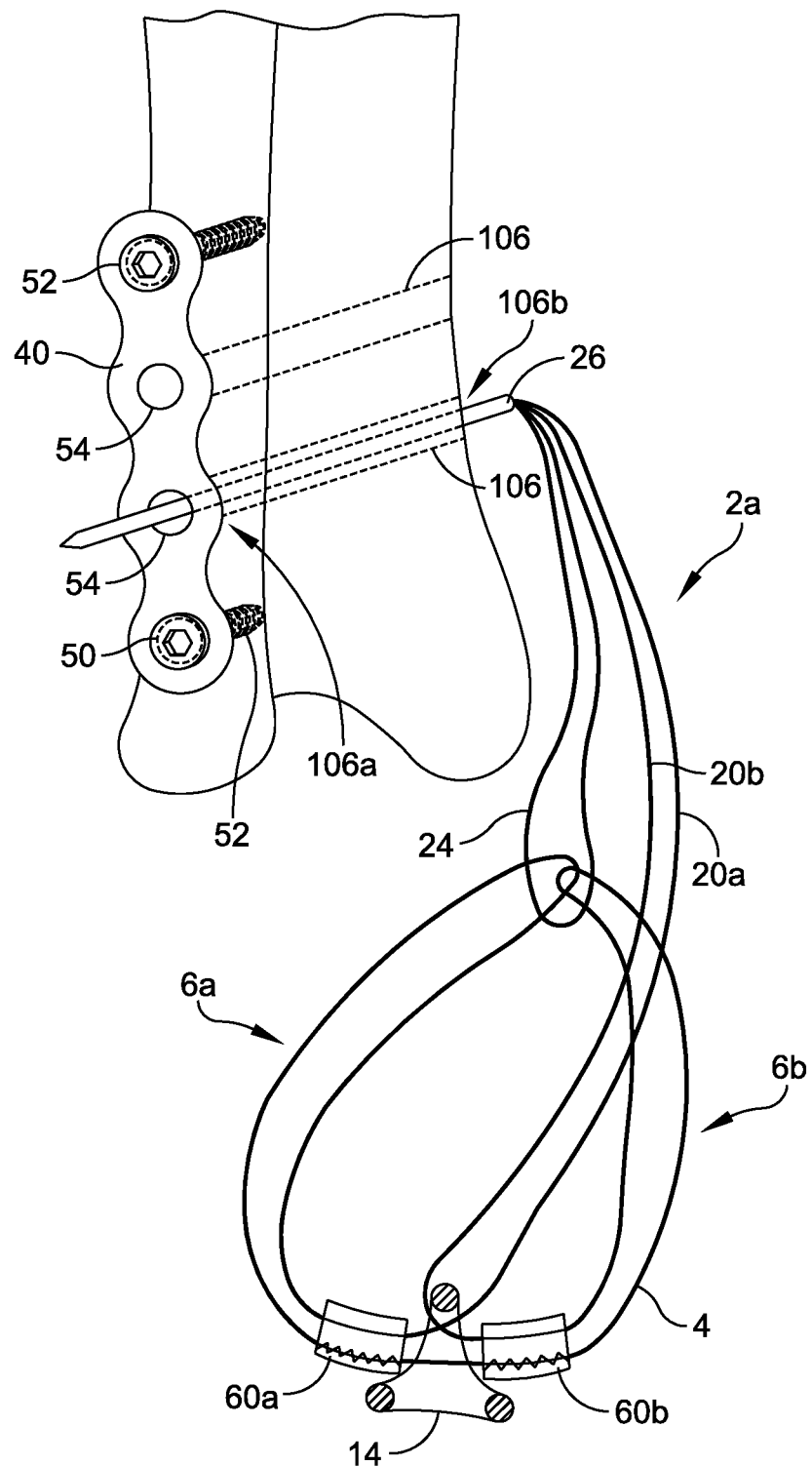
FIG. 10 illustrates the surgical site of FIG. 7 having the anchoring system inserted through the second bone prior to insertion through the first bone, in accordance with some embodiments.
Figure 11:
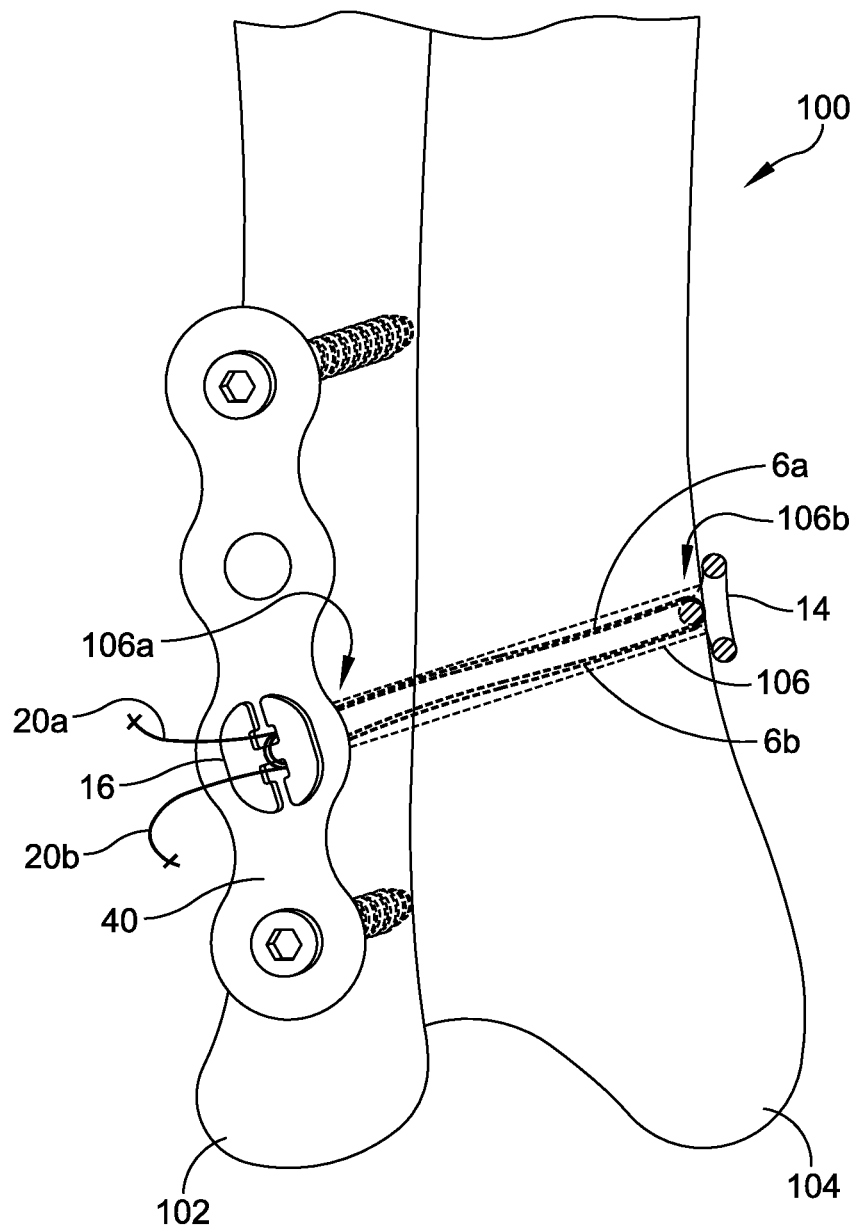
FIG. 11 illustrates the surgical site of FIG. 10 having a first anchor abutting a second bone and a second anchor abutting a first bone, in accordance with some embodiments.

FIG. 8 illustrates a second anchor 16 coupled to a second end 10 of each of the adjustable loops 6a, 6b after the adjustable loops 6a, 6b are passed through the bone tunnel 106. In the illustrated embodiment, the pull-through suture 24 has been previously cut to disconnect the pull-through suture 25 from the adjustable loops 6a, 6b and the adjustable loops 6a, 6b have been advanced into the bone tunnel 106 a sufficient distance such that the first anchor 14 is positioned flush against the bone plate 40. As shown in FIG. 9, the guide element 26 and the pull-through strand 24 are disconnected from the adjustable loops 6a, 6b and the free ends 20a, 20b of the adjustable loops 6a, 6b can be used to tighten (e.g., shorten) the adjustable loops 6a, 6b to position the first anchor 14 and the second anchor 16 against the bone plate 40 and the second bone 104, respectively. In some embodiments, the free ends 20a, 20b can be cut from (or otherwise released from) the guide element 26 prior to tightening of the adjustable loops 6a, 6b. In other embodiments, the free ends 20a, 20b can be tightened by pulling the guide element 26 in a direction away from the first bone 102 and/or the second bone 104. The adjustable loops 6a, 6b maintain the first bone 102 and the second bone 104 at a predetermined spacing and/or within a predetermined range of motion. FIGS. 10-11 illustrate the syndesmotic repair system 2a inserted from a second side 106b of a bone tunnel 106 to a first side 106a.

For example, as shown in FIG. 10, the guide element 26 may be passed from the second side 106b of the bone tunnel 106 to the first side 106a such that the guide element 26 extends out of the bone tunnel 106 and through a construct hole 54 formed in bone plate 40. The free ends 20a, 20b and the pull through suture 24 are further passed from the second end 106b to the first end 106a of the bone tunnel. The free ends 20a, 20b extend from the bone tunnel 106 and through the construct hole 54. The guide element 26 and/or the pull-through suture 24 can be advanced further from the bone tunnel 106 such that a second end 10 of each of the adjustable loops 6a, 6b extends from a first end 106a of the bone tunnel 106.

As shown in FIG. 11, the adjustable loops 6a, 6b can be advanced and/or adjusted such that the first anchor 14 abuts the second bone 104 adjacent to a second end 106b of the bone tunnel 106. A second anchor 16 can be coupled to the second end 10 of the adjustable loops 6a, 6b. The guide element 26 and the pull-through strand 24 are disconnected from the adjustable loops 6a, 6b and the free ends 20a, 20b of the adjustable loops 6a, 6b can be used to tighten (e.g., shorten) the adjustable loops 6a, 6b to position the first anchor 14 and the second anchor 16 against the the second bone 104 and the bone plate 40, respectively. The guide element 26 and/or the pull-through strand 24 can be removed prior to, during, and/or after coupling of the second anchor 16 to the adjustable loops 6a, 6b and/or after tightening of the adjustable loops 6a, 6b. As the adjustable loops 6a, 6b are tightened, the second anchor 16 is positioned against the bone plate 40, for example, within a countersink defined by construct hole 54.

Figure 14:
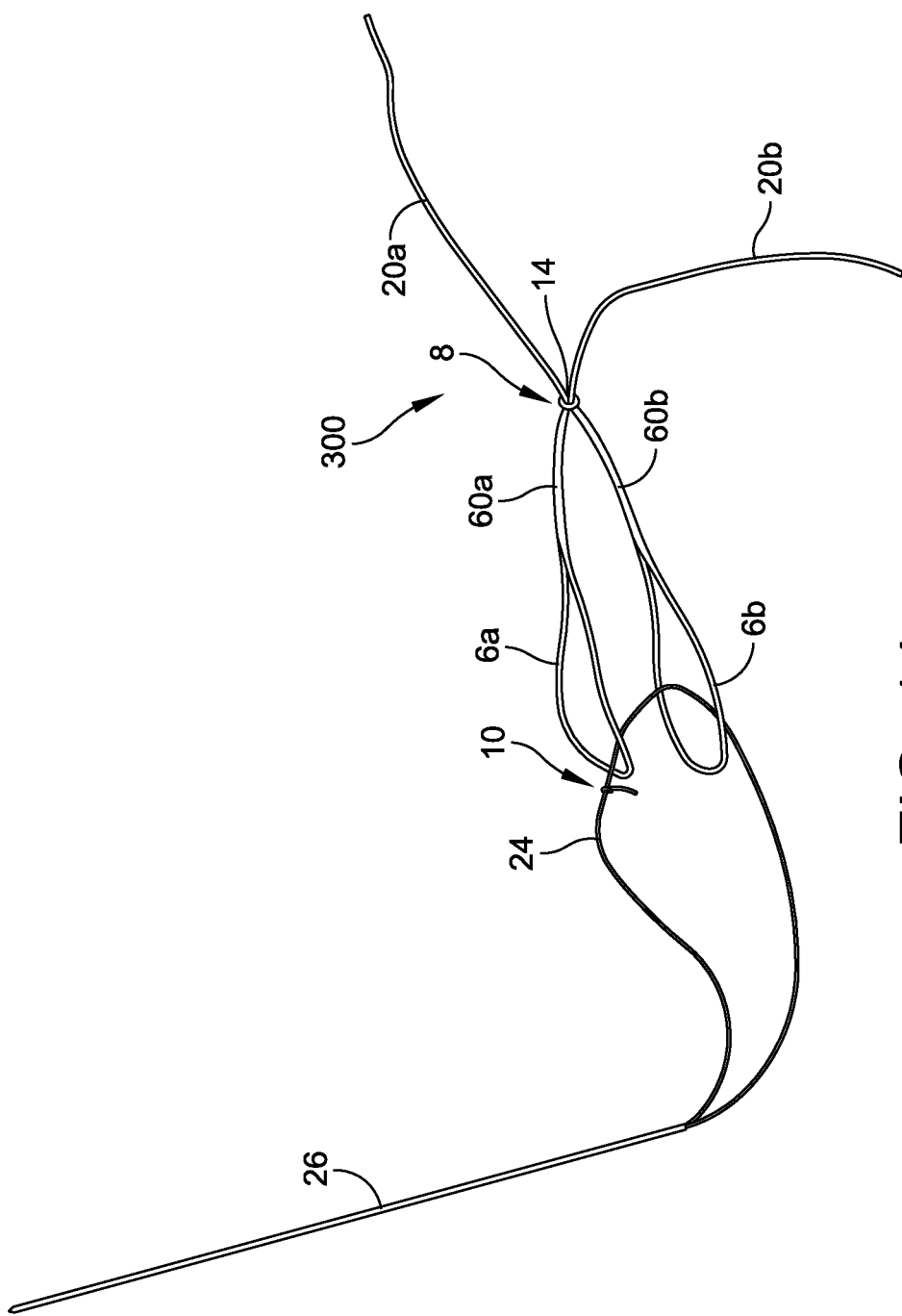
FIG. 14 illustrates a partial anchoring construct including a first independent adjustable loop and a second independent adjustable loop, in accordance with some embodiments.

FIG. 14 illustrates a partial anchoring construct 30d including a first independent adjustable loop 6a and a second independent adjustable loop 6b, in accordance with some embodiments. The partial anchoring construct 30d is similar to the partial anchoring construct 30 described above, and similar description is not repeated herein. The partial anchoring construct 30d includes a flexible strand 4 defining a first independent adjustable loop 6a and a second independent adjustable loop. The first and second independent adjustable loops 6a, 6b are separately formed and do not overlap. In some embodiments, each of the first and second independent adjustable loops 6a, 6b are coupled to a pull-through strand 24.

In some embodiments, each of the independent adjustable loops 6a, 6b are formed by passing a free end 20a, 20b of the flexible strand 4 respectively through a first woven passage 60a and a second woven passage 60b. In the illustrated embodiment, the woven passages 60a, 60b are positioned on the same side of a first anchor 14 as the independently adjustable loops 6a, 6b and are configured to be inserted into a bone tunnel 106. In other embodiments, the woven passages 60a, 60b can be positioned opposite independent the adjustable loops 6a, 6b. The first free end 20a is configured to adjust the first independent adjustable loop 6a and the second free end 20b is configured to adjust the second independent adjustable loop 6b. Each of the free ends 20a, 20b extend on an opposite side of the first anchor 14 from the independent adjustable loops 6a, 6b.

Figure 15:
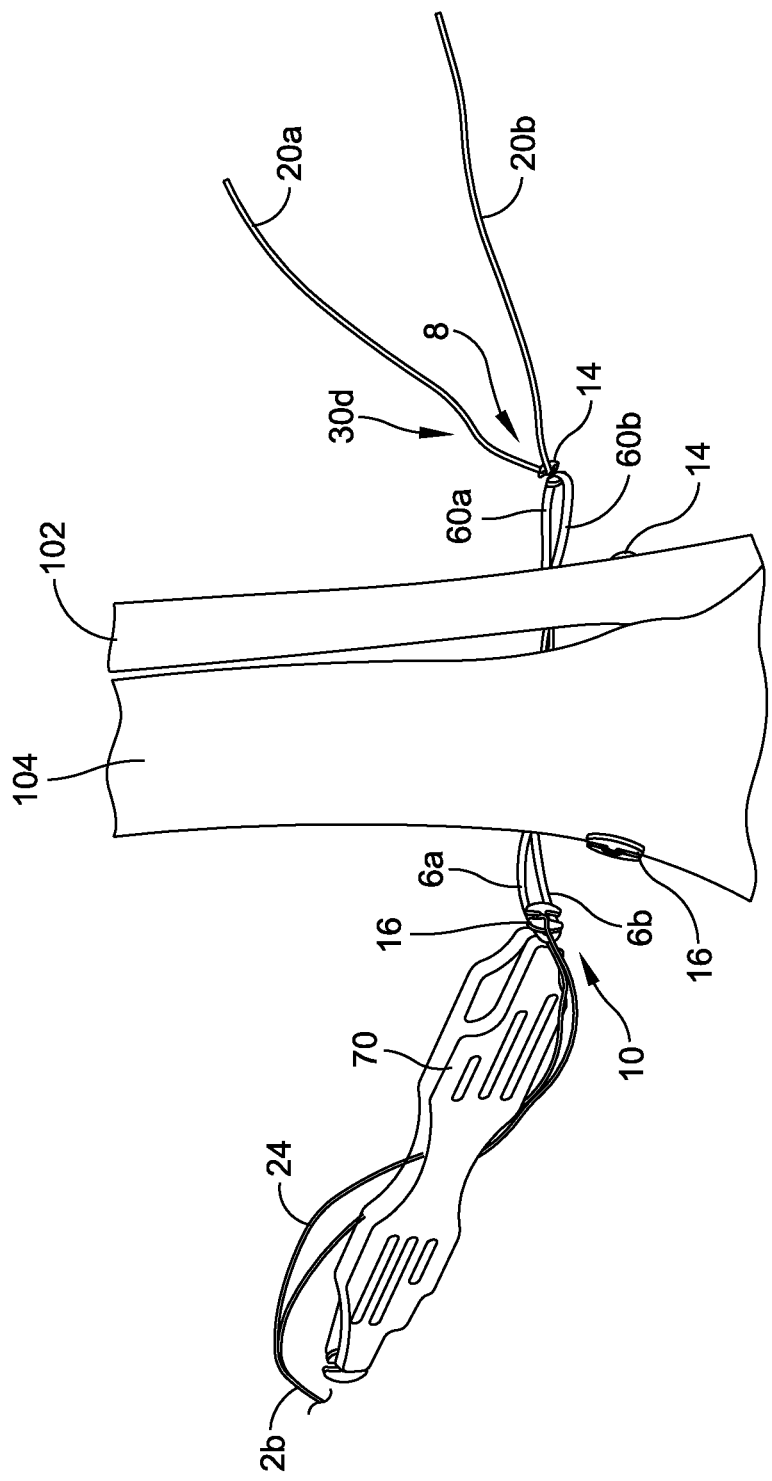
FIG. 15 illustrates the partial anchoring construct of FIG. 14 inserted through a bone tunnel defined in a first bone and a second bone and having a second anchor coupled to a second end of each of the first independent adjustable loop and the second independent adjustable loop, in accordance with some embodiments.

FIG. 15 illustrates the partial anchoring construct 30d of FIG. 14 inserted through a bone tunnel 106 defined in a first bone 102 and a second bone 104 and having a second anchor 16 coupled to a second end 10 of each of the first independent adjustable loop 6a and the second independent adjustable loop 6b, in accordance with some embodiments. As shown in FIG. 15, both independent adjustable loops 6a, 6b are passed through the bone tunnel 106 and coupled to the second anchor 16. The second anchor 16 can be coupled to the independent adjustable loops 6a, 6b using an anchor holder 70. The anchor holder 70 is configured to allow a surgeon to manipulate the second button 16 to couple the second button 16 to the second end 10 of each of the independent adjustable loops 6a, 6b.

As further shown in FIG. 15, the free ends 20a, 20b of each of the independent adjustable loops 6a, 6b extend from the first anchor 14 and are not inserted through or into the bone tunnel 106. After coupling the second button 16 to each of the independent adjustable loops 6a, 6b, the free ends 20a, 20b can be pulled away from the first and second bones 102, 104 to tighten the independent adjustable loops 6a, 6b and position the first anchor 14 and the second anchor 14 against the first and second bone 102, 104, respectively. As shown in FIG. 15, in some embodiments, multiple partial anchoring constructs 30d can be inserted through multiple bone tunnels 106 and coupled to multiple second anchors 16 to position the first bone 102 and the second bone 104 at a predetermined spacing.

FIG. 12 is a flowchart illustrating a method 200a of syndesmotic repair using the syndesmotic system 2a described above in conjunction with FIGS. 7-10, in accordance with some embodiments. The method 200a is similar to the method 200 described above in conjunction with FIG. 6, and similar description is not repeated herein. At step 220, a bone plate 40 is coupled to the first bone 102. In some embodiments, the bone plate 40 is coupled to the first bone 102 by a fastener 52 inserted through at least one fastener hole 50 formed in the bone plate 40. The fastener 52 can include any suitable fastener, such as a screw, pin, k-wire, etc. configured to couple the bone plate 40 to the first bone 102. The bone plate 40 is coupled to the first bone 102 such that at least one construct hole 54 is aligned with the bone tunnel 106 formed through the first and second bones 102, 104.

At step 204a, the guide element 26 is passed through a construct hole 54 formed in the bone plate 40 and through the bone tunnel 106. The construct hole 54 is sized and configured to allow passage of the guide element 26 and the adjustable loop 6 but prevent passage of the first anchor 14 therethrough. In some embodiments, the construct hole 54 includes a countersink sized and configured to receive the first anchor 14 therein. The method 200a proceeds similar to the method 200 after insertion of the partial anchoring construct 30 through the construct hole 54.

Figure 13:
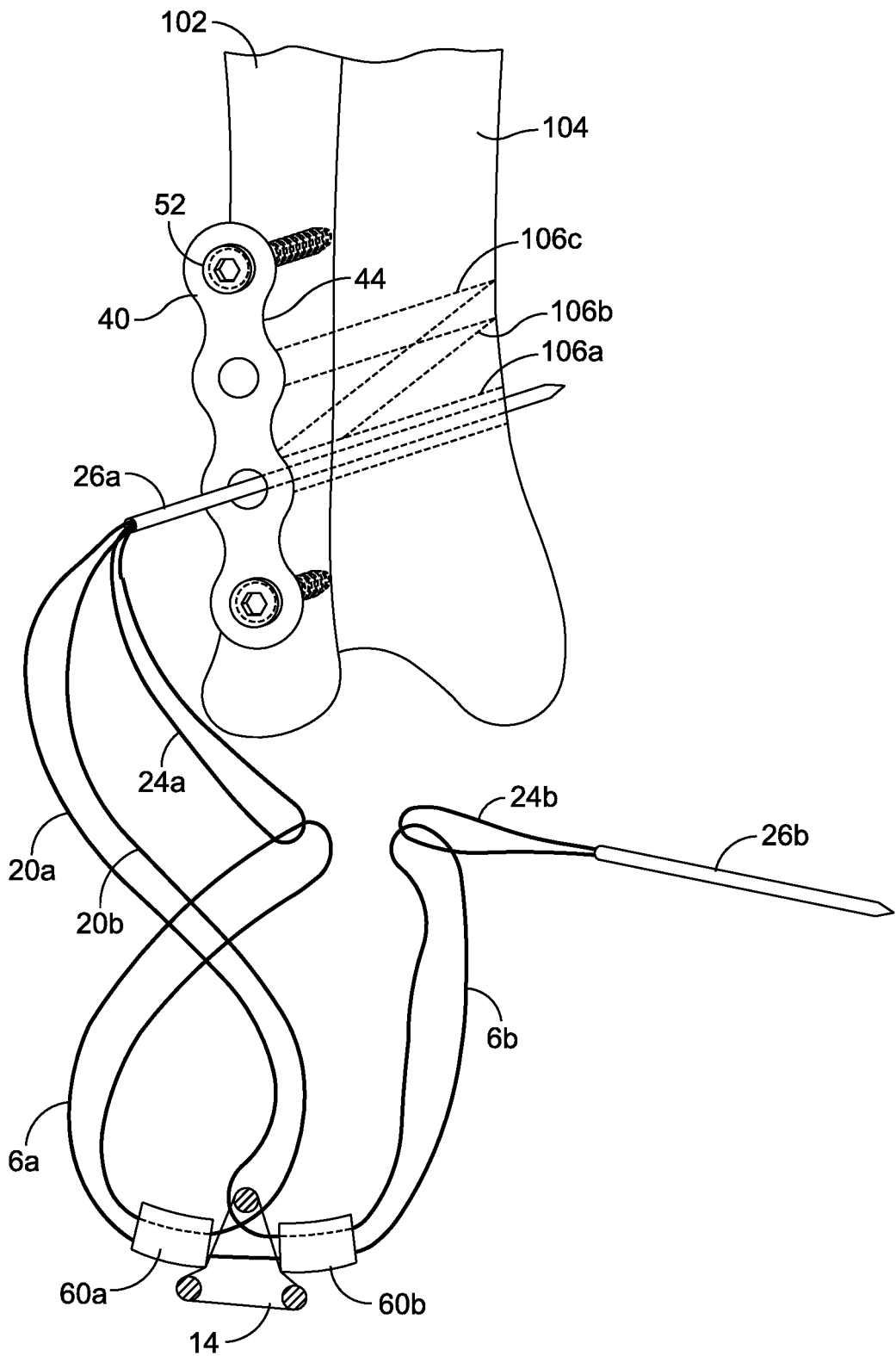
FIG. 13 illustrates a surgical site having an anchoring system including a partial anchoring construct having a first adjustable loop and a second adjustable loop each coupled to a guide element, in accordance with some embodiments.

FIG. 13 illustrates a partial anchoring construct 30c including a first adjustable loop 6a and a second adjustable loop 6b, in accordance with some embodiments. The partial anchoring construct 30c is similar to the partial anchoring construct 30 described above, and similar description is not repeated herein. The first adjustable loop 6a and the second adjustable loop 6b each extend from a first end 8 coupled to a first anchor 14. The adjustable loops 6a, 6b can be formed from a single flexible strand 4 and/or can be formed from multiple flexible strands coupled to the first anchor 14 of the partial anchoring construct 30b.

As illustrated in FIG. 13, in some embodiments, the first adjustable loop 6a is configured to extend through a first bone tunnel and the second adjustable loop 6b is configured to extend through a second bone tunnel. A second end 10a of the first adjustable loop 6a is coupled to a first guide element 26a and the second end 10b of the second adjustable loop 6b is coupled to a second guide element 26b. The first guide element 26a is configured to pass the first adjustable loop 6a through a first bone tunnel and the second guide element 26b is configured to pass the second adjustable loop 6b through the second bone tunnel. In some embodiments, the first guide element 26a is inserted through the first bone tunnel prior to the second guide element 26b being inserted through the second bone tunnel, although it will be appreciated that the second guide element 26b can be inserted before, simultaneously with, or after insertion of the first guide element 26a. After inserting the first and second guide elements 26a, 26b through respective bone tunnels 106a, 106b, a second anchor 16a is coupled to the second end 10a of the first adjustable loop 6a and a second anchor 16b is coupled to the second end 10b of the second adjustable loop 6b. The first and second adjustable loops 6a, 6b can be shortened simultaneously and/or independently to position the first bone 104 and the second bone 106 in a predetermined spacing.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
a first flexible strand defining a first adjustable loop extending between a first end and a second end, wherein the first flexible strand defines a first strand passage and a second strand passage, wherein the first strand passage and the second strand passage have a predetermined spacing, and wherein each of the first strand passage and the second strand passage are sized and configured to receive a portion of the first flexible strand therethrough;
a first anchor coupled to the first end of the first adjustable loop, the first anchor comprising one or more cutouts sized to prevent the first strand passage and the second strand passage from passing therethrough;
a first pull-through strand coupled to the first adjustable loop defined by the first flexible strand, wherein the pull-through strand is configured to pass the first flexible strand through a bone tunnel.

2. The system of claim 1, wherein the first strand passage is positioned adjacent to the first anchor on a first side and the second strand passage is positioned adjacent to the first anchor on a second side.

3. The system of claim 1, wherein the one or more cutouts comprises a first cutout and the first anchor further comprising a base and an extension extending from a first portion of the base to a second portion of the base to define the first cutout between the extension and the base.

4. The system of claim 1, further comprising a second anchor configured to be coupled to the second end of the first adjustable loop after insertion of the first adjustable loop through a bone tunnel.

5. The system of claim 4, wherein the second anchor is selected from the group consisting of a button, a knot capsule, and a screw.

6. The system of claim 1, further comprising a plate defining at least one hole sized and configured to receive the first flexible strand and the pull-through strand therethrough, wherein the plate is configured to couple to a one of the first bone or the second bone.

7. The system of claim 1, wherein at least one of the first strand passage and the second strand passage comprise a woven channel along a length thereof and formed in the first flexible strand.

8. The system of claim 1, wherein the first adjustable loop comprises a first loop and a second loop, and a first free end of the first flexible strand is passed through the first strand passage to define the first loop and a second free end of the first flexible strand is passed through the second strand passage to define the second loop.

9. The system of claim 8, wherein the first free end and the second free end are at the first end of the first adjustable loop and the first loop is coupled to the second loop at the second end of the first adjustable loop.

10. The system of claim 9, wherein the first pull-through strand is coupled to the first adjustable loop at the second end of the first adjustable loop.

11. The system of claim 10, further comprising a guide element configured to pass the first adjustable loop through the bone tunnel, wherein the first free end, the second free end, and the first pull-through strand are configured to pass through the bone tunnel before the first loop and the second loop, by being directly coupled to or integral with the guide element.

12. The system of claim 1, comprising a second flexible strand defining a second adjustable loop extending between a first end and a second end, wherein the second flexible strand defines a first strand passage and a second strand passage, wherein the first strand passage and the second strand passage have a predetermined spacing, and wherein each of the first strand passage and the second strand passage are sized and configured to receive a portion of the second flexible strand therethrough.

13. The system of claim 1, wherein at least one of the one or more cutouts is formed as a slot having an open end configured to receive a portion of the first adjustable loop therethrough.

14. A system, comprising:
   a partial anchoring construct, comprising:
      a first flexible strand defining a first adjustable loop extending between a first end and a second end, wherein the first flexible strand defines a first strand passage and a second strand passage, wherein the first strand passage and the second strand passage have a predetermined spacing, and wherein each of the first strand passage and the second strand passage are sized and configured to receive a portion of the first flexible strand therethrough;
      a first anchor coupled to the first end of the first adjustable loop, the first anchor comprising one or more cutouts sized to prevent the first strand passage and the second strand passage from passing therethrough; and
      a first pull-through strand coupled to the first adjustable loop defined by the first flexible strand, wherein the pull-through strand is configured to pass the first flexible strand through a bone tunnel in a first bone; and
   a second anchor, separate from the partial anchoring construct and configured to be coupled to the second end of the first adjustable loop, the second anchor comprising one or more cutouts formed as a slot having an open end configured to receive a portion of the first adjustable loop therethrough after insertion of the first adjustable loop through a bone tunnel.

15. The system of claim 14, wherein the one or more cutouts comprises two cutouts.

16. The system of claim 14, wherein shortening of the first adjustable loop shortens a spacing between the first anchor and the second anchor.

17. A system, comprising:
   a first flexible strand defining a first adjustable loop extending between a first end and a second end, wherein the first flexible strand defines a first strand passage and a second strand passage, wherein the first strand passage and the second strand passage have a predetermined spacing, and wherein each of the first strand passage and the second strand passage are sized and configured to receive a portion of the first flexible strand therethrough;
   a first anchor coupled to the first end of the first adjustable loop, the first anchor comprising one or more cutouts sized to prevent the first strand passage and the second strand passage from passing therethrough;
   a first pull-through strand coupled to the first adjustable loop defined by the first flexible strand, wherein the pull-through strand is configured to pass the first flexible strand through a bone tunnel in a first bone; and
   a plate defining at least two holes, the at least two holes comprising a first hole sized and configured to receive a fastener therethrough to couple the plate to the first bone and a second hole sized and configured to be concentric with the bone tunnel and to receive the first flexible strand and the pull-through strand therethrough,
   wherein the first anchor is sized such that the first anchor is unable to pass through the second hole in the plate when the first flexible strand and the pull-through strand are pulled through.

* * * * *